United States Patent [19]

Barber

[11] Patent Number: 4,537,232

[45] Date of Patent: Aug. 27, 1985

[54] FLUID DISCRIMINATING APPARATUS

[76] Inventor: Michael F. Barber, 177 Richmond Hill, New Canaan, Conn. 06840

[21] Appl. No.: 596,544

[22] Filed: Apr. 4, 1984

Related U.S. Application Data

[63] Continuation-in-part of Ser. No. 481,793, Apr. 4, 1983.

[51] Int. Cl.$^3$ .............................................. G01N 9/00
[52] U.S. Cl. ...................................... 141/382; 137/2; 222/63
[58] Field of Search .............. 73/32 R, 451, 453, 440; 137/2, 91; 141/94, 192, 311 R, 323, 349, 382, 383; 222/23, 52, 55, 58, 63; 340/603, 619, 624

[56] References Cited

U.S. PATENT DOCUMENTS

| | | | |
|---|---|---|---|
| 2,717,990 | 9/1955 | Person | 340/624 |
| 2,812,773 | 11/1957 | McGee | 137/2 X |
| 3,140,740 | 7/1964 | LaGreid et al. | 126/93 X |
| 3,428,074 | 2/1969 | Perren | 340/619 X |
| 3,882,887 | 5/1975 | Rekai | 340/619 X |
| 3,942,564 | 3/1976 | Nakazato | 141/311 R X |
| 4,134,022 | 1/1979 | Jacobsen | 340/619 X |
| 4,361,835 | 11/1982 | Nagy | 340/624 |
| 4,422,085 | 12/1983 | Sumitomo et al. | 73/453 X |

Primary Examiner—Stephen Marcus
Assistant Examiner—Mark Thronson
Attorney, Agent, or Firm—St. Onge, Steward, Johnston & Reens

[57] ABSTRACT

Apparatus is disclosed for discriminating between desired and undesired fluids such as kerosene. The apparatus is especially adapted for improving the safety of kerosene heaters by discriminating between kerosene suitable for heater use and more volatile materials such as gasoline. Structure is disclosed to terminate flow of fluid to a kerosene heater in response to the sensed presence of a fluid other than kerosene. According to a preferred form of the apparatus, additional structure is provided to prevent fueling a kerosene heater by structure other than that operatively associated with fluid discriminating structure. According to the more specific aspects of the fluid discriminator, a float including magnetic or light-responsive actuators is calibrated to permit or cease the supply responsive to the position of the float in the fluid. A fluid less dense than kerosene, such as gasoline, will cause the float to sink within the fluid and thereby terminate the flow of fluid to the kerosene heater.

14 Claims, 12 Drawing Figures

FLUID DISCRIMINATING APPARATUS

This is a continuation-in-part of Ser. No. 481,793, filed Apr. 4, 1983.

DESCRIPTION

TECHNICAL FIELD

My invention relates to fluid discriminating devices in general, and particularly to those which can be employed to assure the relative safety which kerosene heaters promise when properly used.

Kerosene space heaters are becoming increasingly popular for use in augmenting home central heating systems, heating large open areas on an intermittent basis, and providing emergency heat. The desirability of kerosene heaters is fostered in part due to the low cost of kerosene and the portability of the heaters themselves. Kerosene is especially suited for use in space heaters because of its relatively high heating capacity, its low cost, its ability to burn cleanly, and its relatively low flammability as compared to more volatile fuels such as gasoline.

Unfortunately, despite numerous warnings to the contrary, both by manufacturers and in the press, it sometimes happens that a fluid fuel other than kerosene suitable for heater use is employed instead of or is comingled with kerosene. Where the contaminating fuel happens to be a highly volatile and flammable material such as gasoline, the results can be disastrous. Thus, despite the relative saftey of kerosene itself, the safety consciousness of the public and the industry in general and the many safety-oriented improvements which have been made in kerosene heaters in recent years, there remains a lingering problem which threatens to deny fulfillment of the promise of safety which is offered by kerosene heaters.

In addition to kerosene heaters, there are many other environments where it would be desirable to detect the presence of contaminating fluids. Among these is the fueling of aircrafts where the presence of water can cause engine problems.

BACKGROUND ART

Kerosene heaters are conventionally fueled by portable electric pumps, funnels or hand-held siphon devices. Typically, the pumps and siphons contain downwardly depending tubes which can be extended into a kerosene storage vessel to withdraw a desired amount of kerosene. The kerosene can be passed directly into the kerosene heater, or it can be held in an intermediate storage vessel for transporting from an outside storage drum to a kerosene heater within a building. Regardless of the precise kerosene supply means employed, I am aware of no apparatus which is available for protecting against the presence of highly-combustible fuels such as gasoline. The prior art has suggested a wide variety of means for discriminating between various types of fluids in general; however, I am aware of no prior art teaching which effectively employs any type of fluid discriminator with a keosene heater to solve the problems addressed by me.

In addition to the need for a device for discriminating between fluids such as kerosene suitable for heater use, contaminants, such as more flammable materials, there is a further need for a fail-safe fueling device which would prevent the intentional as well as unintentional addition of a fluid other than desired into a device, e.g. other than kerosene into a kerosene heater. Again, according to my knowledge, the prior art has not offered any solution to this significant problem. It remains that people failing to heed the warnings provided with kerosene heaters, or believing that they are still capable of using fuels such as gasoline safely, will periodically cause accidents, the results of which will unduly frighten many and deter them from the use of an economical and otherwise safe means of heating.

DISCLOSURE OF THE INVENTION

In accordance with the present invention, I provide an apparatus for fueling kerosene heaters with increased safety, a fluid discriminator means adapted for uses such as with kerosene heaters, and a fluid supply means again having safety as a prime objective and result.

The apparatus for fueling kerosene heaters in accordance with the present invention prevents not only unintentional use of fluids other than kerosene suitable for heater use but also the intentional use of such. This apparatus comprises: (a) a fuel reservoir, adapted for integral use with a kerosene heater, which includes a port for filling said reservoir with kerosene; (b) lock means integral with said port for limiting access therethrough to mating connector means; (c) mating connector means configured to mate with said lock means and provide access through said port; (d) conduit means operatively engaged with said connector for transporting kerosene to said reservoir from a kerosene supply means; (e) kerosene supply means operatively engaged with said conduit means for withdrawing kerosene from a storage vessel and advancing it through said conduit means; and (f) fluid discriminator means operatively engaged with said supply means, for sensing the presence of fluids other than kerosene suitable for heater use and terminating flow in response to the sensed presence of such other fluids.

The apparatus for fueling kerosene heaters, in its broad aspects, is not dependant upon any specific type of fluid discriminator means. Accordingly, while the preferred fluid discriminator means described in accordance with the present invention are specifically shown and described, it is possible to employ other fluid discriminators which may sense differences in density by different hydrometric means or by other means which are known to the art. Exemplary of other hydrometric means is one which comprises float means calibrated to either permit or prevent passage of light from a source to a photoelectric device in response to the density of the fluid. Exemplary of other means are fluid discriminator means which operate on the basis of comparing light refraction patterns. These devices can be used with facility, although they may be somewhat more complex in design and construction. The preferred fluid discriminator means of the present invention have the advantage that accurate sensing of the fluid characteristics can be achieved without passing electrical current through or in close proximity to the fluid.

A preferred fluid discriminator apparatus according to the invention comprises: (a) float means calibrated to float at a predetermined, flow-permitting position in fluid maintained in a storage vessel when said vessel contains fluid of a desired density and to move to a predetermined shut-off position when the density of the fluid meets a predetermined density value different from the desired density; (b) electrical circuit means for providing electric current to fluid supply means; (c)

magnetically-responsive switch means interposed in said electric circuit means; (d) magnet means capable of opening and closing said switch means, said magnet means being integral with said float means and operable with said electric circuit means, said switch means, and said fluid supply means to terminate flow of fluid when said float means floats to said shut-off position.

An alternate fluid discriminator apparatus according to the invention comprises: (a) float means calibrated to maintain its uppermost portion a predetermined distance above the surface of fluid maintained in a storage vessel when said vessel contains fluid of the desired density and to float to a predetermined shut-off position when the density of the fluid meets a predetermined density value different from the desired density; (b) at least one prism capable of total internal reflection positioned within said float means effectively to receive and reflect a beam of collimated light when said float means is not at said shut-off position but to be incapable of reflecting said beam of collimated light when at said shutoff position; (c) means for directing a beam of collimated light toward the prism in a manner effective to be reflected thereby when said float means is not at said shut-off position; and (d) means responsive to interruption of a beam of collimated light reflected from said prism for controlling flow of fluid from said storage vessel.

A fluid discriminator apparatus according to the present invention can be employed separate from a total fuel supply system or apart from even a fuel supply means such as a pump or syphon. However, according to the more preferred aspects of the invention, the fluid discriminator apparatus is employed as part of an apparatus for supplying a fluid of desired density to a device, and most preferably as a part of a total, fail-safe apparatus for fueling kerosene heaters.

An apparatus for supplying kerosene to kerosene heaters according to the present invention preferably comprises: (a) kerosene supply means comprising an electrically-operated pump and an electrical circuit means providing power to said pump for withdrawing kerosene from a storage vessel and advancing it through a conduit means; (b) float means calibrated to float at a predetermined, flow-permitting position in fluid maintained in a kerosene storage vessel when said vessel contains kerosene suitable for heater use and to move to a predetermined shut-off position when the density of the fluid meets a predetermined density value different from that of kerosene suitable for heater use; (c) magnetically-responsive switch means interposed in said electrical circuit means; (d) magnet means capable of opening and closing said switch means, said magnet means being integral with said float means and operable with said kerosene supply means to terminate flow of fluid when said float means floats to said shut-off position.

An alternate apparatus for supplying kerosene to kerosene heaters according to the present invention comprises: (a) kerosene supply means comprising an electrically-operated pump and an electrical circuit providing power to said pump for withdrawing kerosene from a storage vessel and advancing it through a conduit means; (b) float means calibrated to maintain its uppermost portion a predetermined distance above the surface of a fluid maintained in a kerosene storage vessel when said vessel contains kerosene suitable for heater use and to submerge to a lower, shut-off position when the density of the fluid is less than that of kerosene suitable for heater use; (c) tubular guide means adapted to be inserted into the storage vessel and to guide the travel of said float means vertically in response to the level of fluid in said storage vessel and the density of the fluid therein; (d) at least one prism capable of total internal reflection positioned within said float means effectively to receive and reflect a beam of collimated light when said float means is not submerged to said shut-off position but to be incapable of reflecting said beam of collimated light when submerged to said shut-off position; (e) means for directing a beam of collimated light toward the prism in a manner effective to be reflected thereby when said float means is not submerged to said shut-off position; (f) a photoelectric cell responsive to an interruption in the beam of collimated light; and (g) electromechanical switch means responsive to a signal from said photoelectric cell indicating an interruption of the beam of collimated light and operatively connected with said circuit to interrupt power to said pump responsive to a signal from said photoelectric cell.

The term "kerosene suitable for heater use" is defined to mean kerosene having a density within the range commercially accepted as being safe from home kerosene heater use and preferably having an extremely low sulfur content. Typically, the density will be between 40° and 47° Baumé. Preferably, kerosene suitable for heater use will have a density within the range of from about 40° to about 44° Baumé. This is in sharp contrast to the density of gasoline, a much lighter fluid which will typically fall within the range of from about 52° to about 78° Baumé.

Because the most commonly available and frequently misused fuels, e.g. gasoline, are lighter than kerosene suitable for heater use, the drawings and the description of the preferred embodiment which follow are directed to apparatus specific for sensing the presence of such lighter fuels. The apparatus of the present invention is not, however, restricted to sensing the presence of only lighter fuels. The invention is also applicable to sensing the presence of fluids heavier than kerosene suitable for heater use. This embodiment is not specifically shown in the drawings because the principles which apply to this class of fluids are simply those as are specifically shown and described with regard to lower density fluids.

Any given device according to the present invention can be arranged within the teachings set forth to discriminate between fluids which are more dense than kerosene, less dense than kerosene, or either more dense or less dense than kerosene. The arrangement of discriminating means responsive to the presence of fluids both denser than kerosene suitable for heater use or less dense than such, can be achieved, for example, by employing two sets of magnetically-responsive switch means, magnet means, and the like, in the preferred embodiment or two sets of prisms, collimated light producing means and control means responsive to the presence or absence of a reflected light beam, in the alternate embodiment. According to one exemplary situation, the float means would have prisms located not only at the below-described low-density shut-off position, but would have a second set of prisms located at a lower level on the float means and arranged operatively with a source of collimated light and a photoelectric cell such that the reception of the beam of collimated light at the photoelectric cell would stop the flow of fluid. Thus, when a fluid heavier than kerosene suitable for heater use is present, the float will rise to a high-density shut-off position and flow will be terminated. And, when a fluid lighter than kerosene suitable for heater use is present, the float will sink to a low-density shut-off position and flow will also be terminated as specifically shown and described.

BRIEF DESCRIPTION OF THE DRAWINGS

The invention will be further described and its advantages will become more apparent when the following detailed description of the preferred embodiments of the present invention is read in light of the accompanying drawings wherein.

BEST MODE FOR CARRYING OUT THE INVENTION

Figures 1, 2:
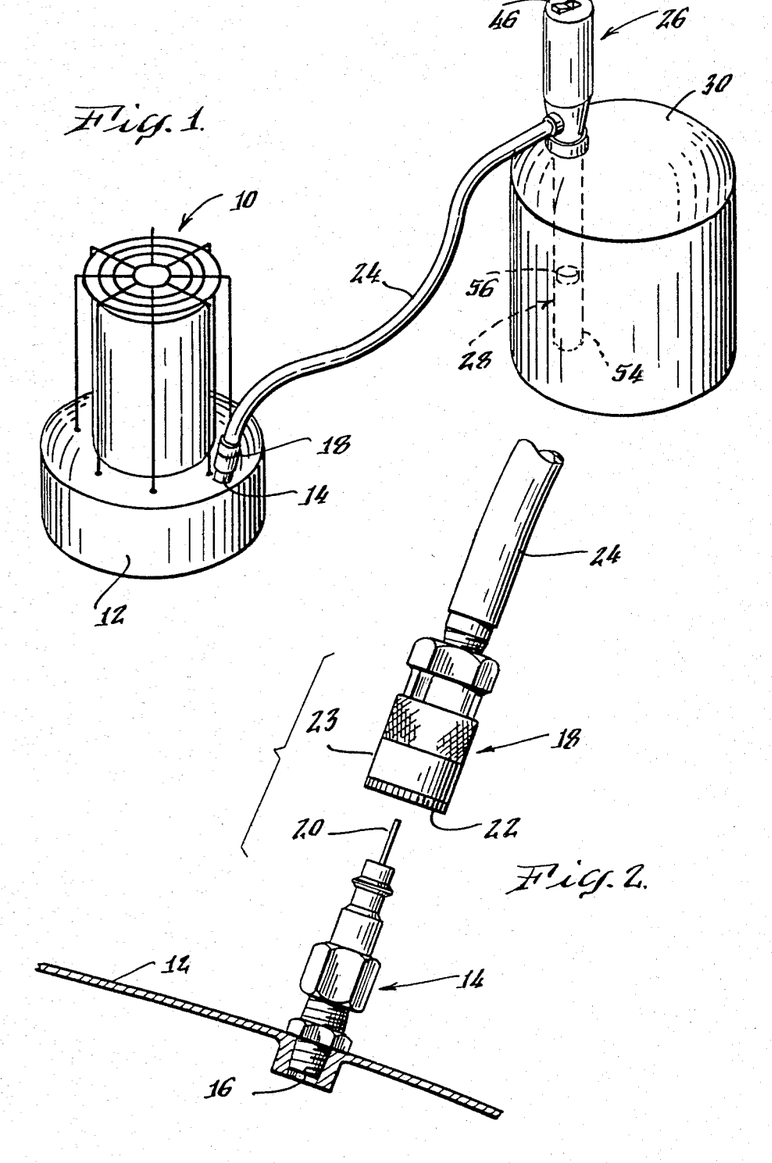
FIG. 1 is a schematic, perspective view showing the major elements of an apparatus for fueling kerosene heaters with improved safety according to the invention.
FIG. 2 shows the exterior detail of a preferred lock means and mating connector means which prevent filling the fuel reservoir unless a fluid discriminator means for sensing the presence of fuels other than kerosene suitable for heater use is employed.

The schematic view of FIG. 1 shows the principal elements of an apparatus for fueling kerosene heaters with improved safety in accordance with the present invention. The kerosene heater 10 includes a fuel reservoir 12 integral with the kerosene heater and in this particular instance forming the base thereof. By the term integral as used in this instance and throughout the description, it is intended to define a necessary component of the subject device in the sense that the device cannot operate unless it is operatively engaged with the integral part. The integral part may be removeable, such as in the case of fuel reservoir 12, to permit filling while not connected to the heater or easy purging in the case of contamination with fluids such as water.

Mounted on the fuel reservoir 12 is a lock means 14 which extends through a port 16 (shown in FIG. 2) within the wall of the reservoir 12. The lock means 14 is integral with the port and has the purpose of limiting access through the port only to suitable fuel supply means by virtue of a mating connector means 18 which is configured to mate with the lock means and provide access through the port. The detailed view of FIG. 2 shows one particularly preferred type of combination lock means and mating connector means. As shown in FIG. 2, the lock means has a male fitting 20 for receipt by a mating female fitting 22 in the connector means 18. A slidable sleeve 23 permits entry of fitting 20 into fitting 22 when drawn upwardly and then locks the two fittings together when brought downwardly again, preferably by a spring-bias action. The relative positions of the male and female members shown in FIG. 2 may be reversed to have a female fitting integral with port 16. Furthermore, it is possible to employ lock means and mating connector means structurally different from those shown in FIG. 2, so long as they have the ability to limit access through the port 16 to only those fuel supply means which are integral with connector means configured to mate with the lock means which are integral with the port 16. By requiring such a mated fitting, the risk that a contaminating fuel will be knowingly or unknowingly supplied to the fuel reservoir 12 is significantly diminished.

Referring again to FIG. 1, conduit means 24 are operatively engaged with the connector 18 for transporting kerosene to the reservoir 12 from a kerosene supply means shown generally as 26. In this particular embodiment, the kerosene supply means is represented as an electrically operated pumping means; however, it is also within the scope of the present invention to provide a hand-operated siphon means of the type presently employed in the art. Operatively engaged with the supply means 26 is a fluid discriminator means shown generally as 28 (in phantom lines) extending vertically into a kerosene storage vessel 30.

Figures 3, 4, 5:
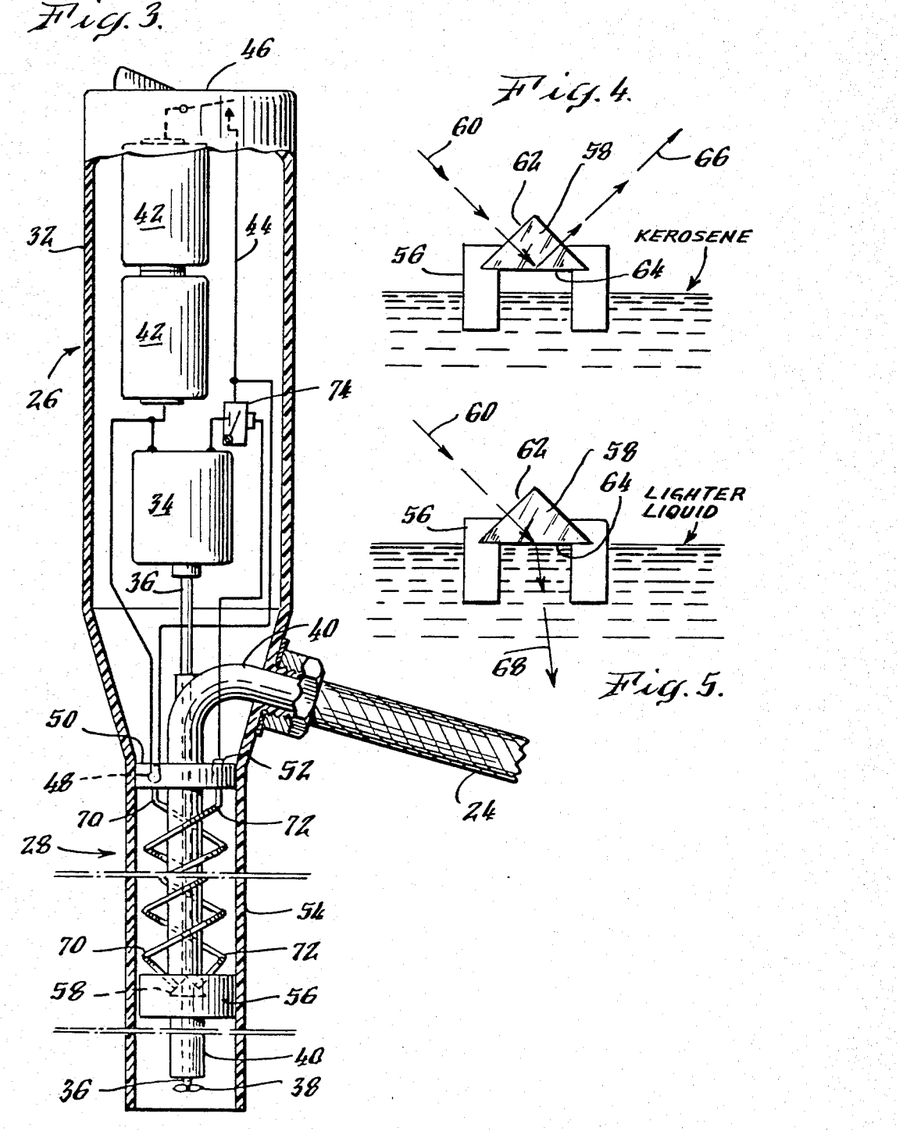
FIG. 3 is a foreshortened sectional view of a fluid supply apparatus according to the present invention employing fluid discriminator means also according to the present invention.
FIGS. 4 and 5 are schematic views representing the principal of operation of a fluid discriminator of the invention which employs a prism capable of total internal reflection.

Referring now to FIG. 3, there is seen a foreshortened view, partially in section of a kerosene supply means 26 with integral fluid discriminating means 28 of the type which is shown generally in FIG. 1. The kerosene supply means 26 is shown to have an outer housing 32 which can be constructed of a suitable impact-resistant plastic or a suitable metal such as stainless steel. An electric motor 34 rotatably drives shaft 36 causing impeller means 38 to rotate and cause fluid to be forced through conduit 40. The fluid in conduit 40 flows vertically upward through the outer housing 32 and into conduit means 24. Power is supplied to motor 34 by an appropriate number of cells 42 through appropriate circuitry 44. An on/off toggle switch 46 controls the supply of electrical power to the motor 34 as well as a light source 48. The light source 48 is shown in its preferred location within a bulkhead 50 which also preferably supports a photoelectric cell 52 which also plays a part in controlling the delivery of power to motor 34 as will be described in more detail below.

The lower portion of outer housing 32 provides a tubular guide means 54 which is adapted to be inserted into a storage vessel, such as 30 shown in FIG. 1, and to guide the travel of a float means such as 56 vertically in response to both the level of fluid in the storage vessel and the density of the fluid therein.

The fluid discriminator means shown generally as 28 is operatively engaged with the supply means shown generally as 26 for sensing the presence of fluids other than kerosene suitable for heater use and terminating flow in response to the sensed presence of such other fluids. In the embodiment shown in FIG. 3, the float means 56 is calibrated to maintain its uppermost portion a predetermined distance above the surface of fluid maintained in a kerosene storage vessel when the vessel contains kerosene suitable for heater use and to submerge to a lower, low-density shut-off position when the density of the fluid is less than that of kerosene suitable for heater use. As indicated in the general remarks above, the float means 56 can also be suitably calibrated to have a high-density shut-off position for sensing and terminating fluid flow when the density of the fluid in the storage vessel is higher than that of kerosene suitable for heater use. The preferred fluid discriminator means according to this embodiment of the present invention will further comprise safety shut-off means associated with the float means 56 for terminating the flow of fluid from the storage vessel when the float submerges to a low-density shut-off position, or when it rises to the high-density shut-off position.

A preferred form of the safety shut-off means according to this embodiment is shown schematically in FIG. 3 and its operation is explained with the aid of FIGS. 4 and 5. Such a shut-off means will preferably comprise at least one prism 58 which is capable of total internal reflection. The prism 58 will be positioned within the float means 56 effectively to receive and reflect a beam of collimated light when the float means is not submerged to said low density shut-off position, but to be incapable of reflecting the beam of collimated light when submerged to that shut-off position.

FIG. 4 schematically shows a collimated beam of light 60 is directed a prism 58 which floating in kerosene suitable for heater use. The light passes through one face 62 of a prism onto an internal surface 64 of the prism which reflects the light totally out of the prism as shown at 66.

FIG. 5 schematically shows the operation of the float when the fluid in which it is held is less dense than kerosene suitable for heater use. In this particular situation, the total internal reflection of the prism is disrupted by the presence of the lighter liquid against surface 64 of the prism and the beam of light is transmitted through the liquid as shown by the arrows 68.

The beam of collimated light can be provided by any suitable means. FIG. 3 shows a light source 48 which provides light which is transmitted through a first fiber optic means 70 to one face of a prism. The fiber optic means 70 is positioned operatively to direct light through one face of the prism toward a second, internal face thereof at an angle effective to cause internal reflection of the light through a third face of the prism when the float is not submerged in said low-density shut-off position. Preferably, a second fiber optic means 72 is positioned operatively to receive light reflected from the second, internal face of the prism and to transmit it to means responsive to interruption of a beam of collimated light.

According to the embodiment shown in FIG. 3, the means responsive to interruption of the beam of collimated light comprise photoelectric cell 52 and electromechanical switch means 74. When the presence of a fluid less dense than kerosene suitable for heater use is present, the float means 56 will sink therein to a low density shut-off position causing an interruption in the light transmitted via fiber optic means 72 to photoelectric cell 52. The electromechanical switch means 74 is operatively connected with the circuit 44 to interrupt power to the pump 34 responsive to a signal from the photoelectric cell 52.

In the alternative embodiment where a hand-operated siphon means is employed in place of the electrically operated pump, the same basic control system as described can be employed with the electromechanical switch means activating a valve operative to terminate siphoning action. This valve can either effect a loss of vacuum in the siphon line or positively close off the siphon line.

Figure 6:
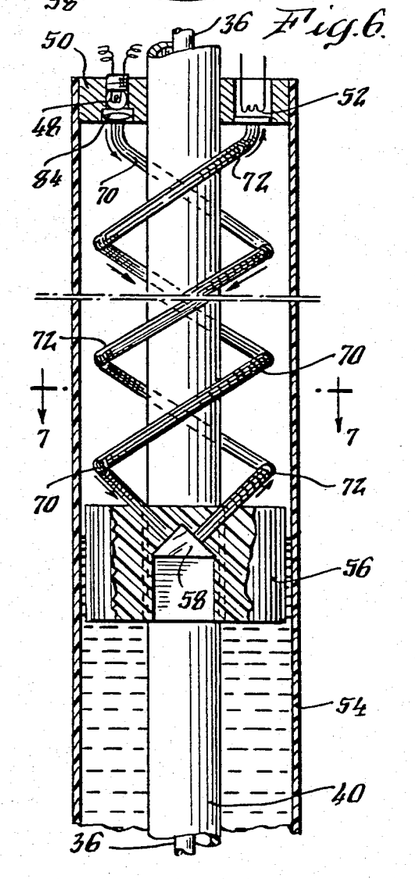
FIG. 6 is a foreshortened view, partially in section, showing an embodiment of a fluid discriminator apparatus in operative position within a fluid supply apparatus according to the present invention.
Figure 7:
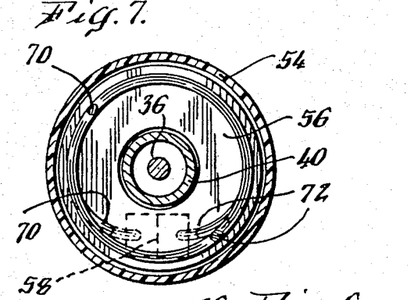
FIG. 7 is a cross-sectional view taken at line 7—7 in FIG. 6.

FIGS. 6 and 7 show in greater detail the embodiment discussed in accordance with FIG. 3. The embodiment of FIG. 6, which can be viewed in cross section in FIG. 7, shows float means 56 centrally positioned within tubular guide means 54 and concentrically with conduit means 40. The prism 58 is located within the float means 56 to one side of the conduit 40. First fiber optic means 70 and second fiber optic means 72 are operatively engaged with the prism 58 and spiral helically around conduit 40 to their points of connection with bulkhead 50 at the light source 48 and the photoelectric cell 52 respectively. This arrangement allows the float means 56 to move vertically within the tubular guide means 54 in response to both the level of fluid therein, which is a function of the level of fluid within the storage vessel such as 30, and the density of that fluid. Thus, the fluid discriminating apparatus according to the present invention will operate effectively regardless of the level of fluid in the storage vessel 30.

Figure 8:
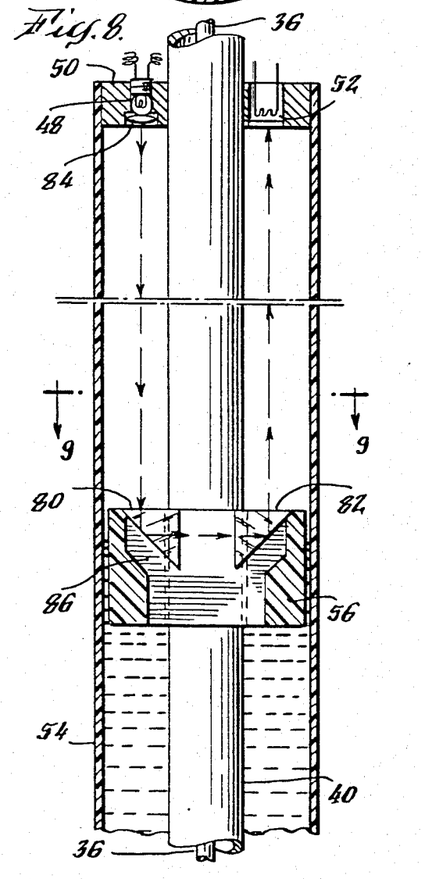
FIG. 8 is a foreshortened view, partially in section, showing another embodiment for a fluid discriminator apparatus in place in a fluid supply apparatus according to the invention.
Figure 9:
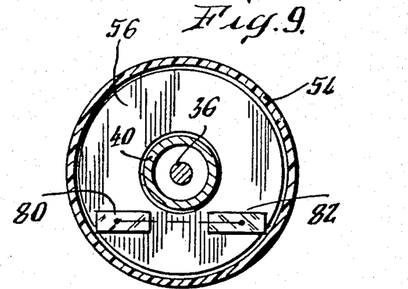
FIG. 9 is a cross-sectional view taken at line 9—9 in FIG. 8.

FIGS. 8 and 9 show an alternative embodiment of the invention which employs at least two prisms 80 and 82, both capable of total internal reflection, which are positioned within the float means in a manner which effectively eliminates the need for fiber optic means 70 and 72 as shown in the embodiment of FIG. 6. According to the embodiment of FIGS. 8 and 9, the light source 48 has associated with it a lens means 84 which projects a beam of collimated light toward the upper surface of prism 80 for internal reflection toward the vertical surface of prism 82. Prism 82 then reflects the light vertically upwardly to photoelectric cell 52. In this instance, the float means 56 is calibrated to sink within a fluid less dense than kerosene suitable for heater use to an extent that annular cavity 86 becomes filled with fluid, thereby eliminating the internal reflection of the beam of light and interrupting the beam of light at photoelectric cell 52.

Figures 10, 11, 12:
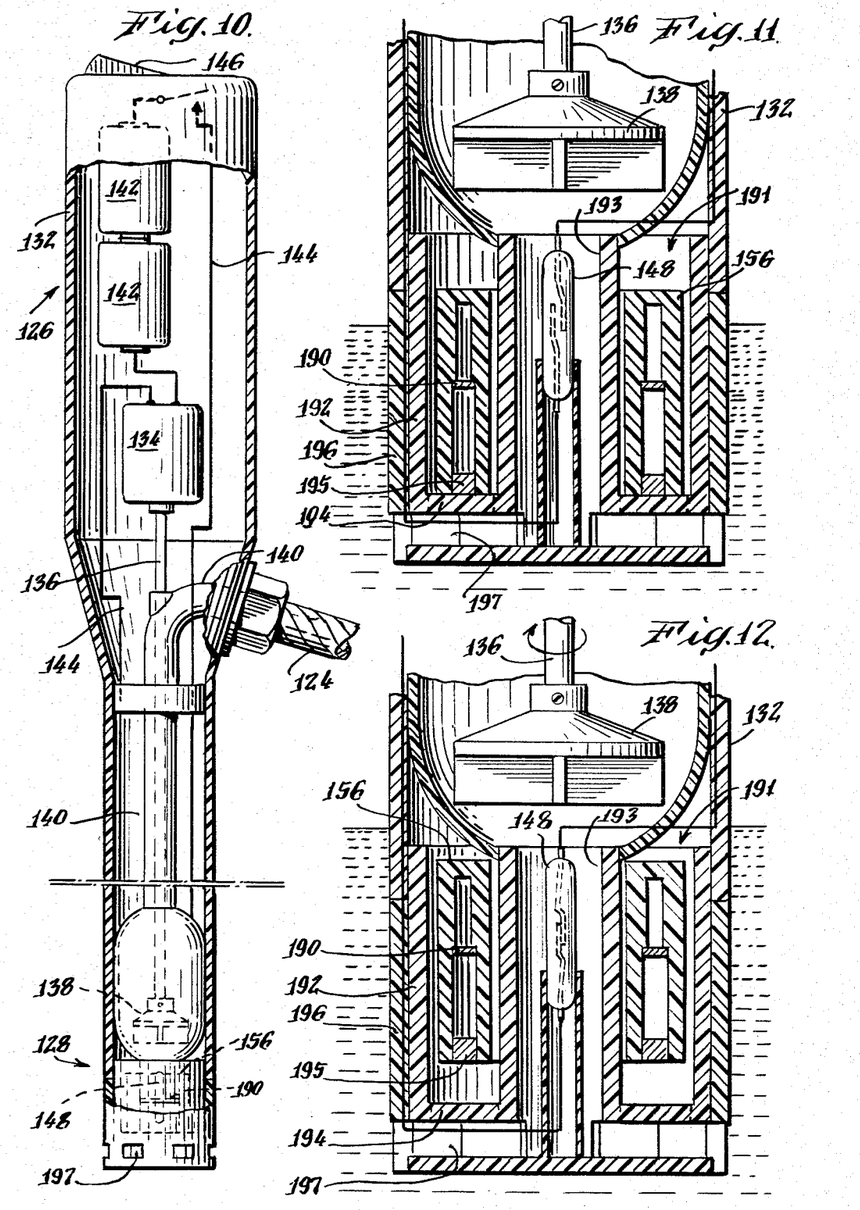
FIG. 10 is a foreshortened sectional view of a fluid supply apparatus according to the present invention employing a more preferred discriminator means according to the invention.
FIG. 11 is a sectional view of the lower portion of the device shown in FIG. 10, showing a float means carrying a magnet which is positioned in the shut-off position.
FIG. 12 is a sectional view similar to that of FIG. 11, but showing the float means with integral magnet positioned in flow-permitting position.

Reference is now made to FIGS. 10 through 12 which illustrate what is currently the preferred fluid discriminating apparatus according to the invention. FIG. 10 shows a foreshortened view, partially in section, of a kerosene supply means 126 with integral fluid discriminating means 128, again of the type generally shown in FIG. 1. The reference numerals in FIGS. 10 through 12 will be three digit numbers which will have the same last two digits as equivalent parts described above with reference to the other Figures. The functions and interrelationship of all of these parts will thus not be repeated in its entirety here.

The kerosene supply means 126 is shown to have an outer housing 132 which encloses the fluid discriminator means 128 as well as an electric motor 134 for rotatably driving shaft 136 and associated impeller means 138 for causing fluid to flow up through conduit 140, and associated electrical circuit and power means. Power in the form of electrical current is supplied to motor 134 by an appropriate number of dry cells 142 through electrical circuit means 144. On/off toggle switch 146 is interposed in circuit 144 as is a magnetically-responsive switch means 148. Current will flow when both switches are closed, but will be interrupted when either is open. The magnetically-responsive switch means 148 is shown as a normally-open reed switch sealed in a glass bulb.

Float means 156 is calibrated to float at a predetermined, flow-permitting position (see FIG. 12) in fluid maintained in a storage vessel when the vessel contains fluid of a desired density, and to move to a predetermined shut-off position (see FIG. 11) when the density value is different from the desired density. According to this embodiment, magnet means 190 is made integral with calibrated float means 156 such that it rises and falls with the float in response to the density of the fluid in which it is inserted. The magnet means 190 are capable of opening (FIG. 11) and closing (FIG. 12) the magnetically-responsive switch means 148. The magnet means 190 are operable with the electric circuit 144, the switch means 148 and fluid supply means (motor 134 in this embodiment) to cause flow of fluid when the float means 156 is at the flow-permitting position and to terminate flow when float means 156 is at the shut-off position.

In this preferred embodiment, as illustrated in FIGS. 10 through 12, the float means 156 is calibrated to be in the flow-permitting position when the vessel contains kerosene suitable for heater use and to submerge to a lower, low-density shut-off position when the density of the fluid is less than that of kerosene suitable for heater use. As indicated above, however, the float means 156 can also be suitably calibrated to have a high-density shut-off position for sensing and terminating fluid flow when the density of the fluid in the storage vessel is higher than that of kerosene suitable for heater use. The most preferred fluid discriminator means will further comprise safety shut-off means associated with the float means 156 for terminating the flow of fluid from the storage vessel when the float submerges to a low-density shut-off position, or when it rises to the high-density shut-off position.

Referring to FIGS. 11 and 12, the detail of the fluid discriminating means can be seen. The float means 156, carrying integral magnet means 190, is of annular shape and is adapted to move vertically in an annular channel defined by inner basket 191. Inner basket is shown to have upstanding cylindrical walls 192 and 193, spaced at the bottom by radial strut numbers 194 which provide proper spacing but still permit fluid to enter the annular opening and contact the float means 156. Ballast means 195 are provided to calibrate float means 156. Inner basket 191 is maintained in proper position by outer basket 196 which includes openings 197 to permit entry of fluid and upstanding support member 198 which holds magnetically responsive switch means 148 in its proper position. As described above, when the float means 156 is in the position shown in FIG. 12, the impeller 138 operates to pump fluid through conduit 140, but when at the position shown in FIG. 11, the electrical circuit is interrupted and flow terminates.

The above description is for the purpose of describing the present invention in terms which will enable those skilled in the art to make and use the same. It is not intended to describe each and every obvious modification and variation of the invention which will become apparent to the skilled worker upon reading the disclosure. Applicant does intend, however, to include such modifications and variations within the scope of the present invention which is defined by the following claims.

I claim:

1. An apparatus for fueling kerosene heaters with improved safety, which comprises:
   (a) a fuel reservoir, adapted for integral use with a kerosene heater, which includes a port for filling said reservoir with kerosene;
   (b) lock means integral with said port for limiting access therethrough to a mating connector;
   (c) said mating connector configured to mate with said lock means and provide access through said port;
   (d) conduit means operatively engaged with said mating connector for transporting kerosene to said reservoir from a supply of kerosene;
   (e) means operatively engaged with said conduit means for withdrawing kerosene from a storage vessel and advancing it through said conduit means; and
   (f) fluid discriminator means, operatively engaged with said withdrawing and advancing means, for sensing the presence of fluids other than kerosene suitable for heater use and terminating flow in response to the sensed presence of such other fluids.

2. An apparatus according to claim 1 wherein the fluid discriminator means comprises:
   (a) a float calibrated to maintain its uppermost portion a predetermined distance above the surface of fluid maintained in a kerosene storage vessel when said vessel contains kerosene suitable for heater use and to submerge to a lower, shut-off position when the density of the fluid is less than that of kerosene suitable for heater use; and
   (b) safety shut-off means associated with said float for terminating flow of fluid from said storage vessel when said float submerges to said shut-off position.

3. An apparatus according to claim 2 wherein said safety shut-off means comprises:
   (a) at least one prism capable of total internal reflection positioned within said float effectively to receive and reflect a beam of collimated light when said float is not submerged to said shut-off position but to be incapable of reflecting said beam of collimated light when said float is submerged to said shut-off position;
   (b) means for directing a beam of collimated light toward the prism in a manner effective to be reflected thereby when said float is not submerged to said shut-off position; and
   (c) means responsive to interruption of a beam of collimated light reflected from said prism for terminating flow of fluid from said storage vessel when said beam is interrupted.

4. An apparatus according to claim 3 wherein said means for directing a beam of collimated light toward said prism comprises fiber optics means positioned operatively to direct light through one face of said prism toward a second, internal face thereof at an angle effective to cause internal reflection of said light through a third face of said prism when said float is not submerged in said safety shut-off position.

5. An apparatus according to claim 4 which further includes second fiber optic means positioned operatively to receive light reflected from said second, internal face of said prism and to transmit it to said means responsive to interruption of a beam of collimated light.

6. An apparatus according to claim 3 wherein said means responsive to interruption of a beam of collimated light comprise a photoelectric cell and an electro-mechanical switch.

7. An apparatus according to claim 6 wherein said withdrawing and advancing means comprises an electrically-operated pump and an electrical circuit providing power to said pump, and wherein said electromechanical switch is operatively connected with said circuit to interrupt power to said pump responsive to a signal from said photoelectric cell.

8. An apparatus according to claim 3 wherein said float is maintained within tubular guide means adapted to be inserted into said storage vessel and to guide the travel of said float vertically in response to the level of fluid in said storage vessel and the density of the fluid therein.

9. An apparatus according to claim 8 which comprises:
at least two prisms capable of total internal reflection positioned within said float, positioned with their internal reflective surfaces at angles with respect to the vertical axis of said tubular guide means effectively to receive in a first prism a vertically downwardly directed collimated light beam, reflect it toward a second prism and then upwardly to said means responsive to interruption of a beam of collimated light.

10. An apparatus for supplying kerosene to kerosene heaters comprising:
(a) means comprising an electrically operated pump and an electrical circuit providing power to said pump for withdrawing kerosene from a storage vessel and advancing it through a conduit;
(b) a float calibrated to maintain its uppermost portion a predetermined distance above the surface of fluid maintained in a kerosene storage vessel when said vessel contains kerosene suitable for heater use and to submerge to a lower, shut-off position when the density of the fluid is less than that of kerosene suitable for heater use;
(c) tubular guide means adapted to be inserted into said storage vessel and to guide the travel of said float vertically in response to the level of fluid in said storage vessel and the density of the fluid therein;
(d) at least one prism capable of total internal reflection positioned within said float effectively to receive and reflect a beam of collimated light when said float is not submerged to said shut-off position but to be incapable of reflecting said beam of collimated light when said float is submerged to said shut-off position;
(e) means for directing a beam of collimated light toward the prism in a manner effective to be reflected thereby when said float is not submerged to said shut-off position;
(f) a photoelectric cell responsive to an interruption in the beam of collimated light; and
(g) an electromechanical switch responsive to a signal from said photoelectric cell indicating interruption of the beam of collimated light and operatively connected with said circuit to interrupt power to said pump responsive to a signal from said photoelectric cell.

11. An apparatus according to claim 10 wherein:
said means for directing a beam of collimated light toward said prism comprises first fiber optics means positioned operatively to direct light through one face of said prism toward a second, internal face thereof at an angle effective to cause internal reflection of said light through a third face of said prism when said float is not submerged in said safety shut-off position; and
the apparatus further includes second fiber optic means positioned operatively to receive light reflected from said second, internal face of said prism and to transmit it to said means responsive to interruption of a beam of collimated light.

12. An apparatus according to claim 10 which comprises:
at least two prisms capable of total internal reflection positioned within said float, positioned with their internal reflective surfaces at angles with respect to the vertical axis of said tubular guide means effectively to receive in a first prism a vertically downwardly directed collimated light beam, reflect it toward a second prism and then upwardly to said means responsive to interruption of a beam of collimated light.

13. An apparatus according to claim 10 which further comprises means cooperative with means on a kerosene heater which limit access to the heater to the defined apparatus for supplying kerosene.

14. An apparatus for supplying kerosene to kerosene heaters comprising:
(a) means comprising an electrically-operated pump and an electrical circuit means providing power to said pump for withdrawing kerosene from a storage vessel and advancing it through a conduit;
(b) means calibrated to float at a predetermined, flow-permitting position in fluid maintained in a kerosene storage vessel when said vessel contains kerosene suitable for heater use and to move to a predetermined shut-off position when the density of the fluid meets a predetermined density value different from that of kerosene suitable for heater use;
(c) a magnetically-responsive switch interposed in said electric circuit means;
(d) a magnet capable of opening and closing said switch, said magnet being integral with said float means and operable with said withdrawing and advancing means to terminate flow of fluid when said float means floats to said shut-off position.

* * * * *